United States Patent [19]

Rothschild et al.

[11] Patent Number: 5,711,973
[45] Date of Patent: Jan. 27, 1998

[54] APPARATUS FOR MAKING A PROSTHETIC SOCKET

[75] Inventors: Vernon R. Rothschild, Berlin; John R. Fox, Trappe; Russell J. Rothschild, Kent Island, all of Md.

[73] Assignee: Rothschild's Orthopedics, Salisbury, Md.

[21] Appl. No.: 637,041

[22] Filed: Apr. 24, 1996

[51] Int. Cl.$^6$ .................. B29C 51/12; A61F 2/80
[52] U.S. Cl. .................. 425/504; 264/573; 425/393; 623/33
[58] Field of Search .................. 623/33; 156/215; 264/573; 425/2, 393, 504

[56] References Cited

U.S. PATENT DOCUMENTS

| | | | |
|---|---|---|---|
| 2,967,563 | 1/1961 | Huff et al. | 156/215 |
| 3,168,604 | 2/1965 | Kramer et al. | 264/573 |
| 3,879,160 | 4/1975 | Miller | 425/393 |
| 4,397,048 | 8/1983 | Brown et al. | 264/258 |
| 4,908,037 | 3/1990 | Ross | 623/32 |
| 4,955,920 | 9/1990 | Wellershaus et al. | 623/36 |
| 5,201,773 | 4/1993 | Carideo, Jr. | 623/32 |
| 5,226,918 | 7/1993 | Silagy et al. | 623/32 |
| 5,376,129 | 12/1994 | Faulkner et al. | 623/33 |
| 5,503,543 | 4/1996 | Laghi | 425/393 |

*Primary Examiner*—Robert Davis
*Attorney, Agent, or Firm*—Sixbey, Friedman, Leedom & Ferguson, P.C.; Gerald J. Ferguson, Jr.; Donald R. Studebaker

[57] ABSTRACT

A method and apparatus for forming a prosthetic socket using a vacuum tube assembly for vacuum sealing a layer of plastic material onto a molded cast to form a prosthetic socket. The vacuum tube assembly includes a cylindrical shaft for providing an air path for the vacuum tube assembly between the prosthetic cast and a suction device. The cylindrical shaft includes a connection device attached to one end of the cylindrical shaft, wherein the connection device is used for affixing the vacuum tube assembly to an attachment device on the prosthetic socket. The attachment device is formed within the prosthetic socket and is the component which connects the prosthetic socket to an artificial limb shaft. A reciprocating cover is also provided on one end of the cylindrical shaft for covering the connection device, so that the reciprocating cover abuts the prosthetic socket when the connection device is affixed to the attachment device. The reciprocating cover is spring-loaded against the cylindrical shaft so that a force is exerted against the reciprocating cover toward the prosthetic socket, wherein a force must be exerted against the cover sufficient enough to overcome the spring-load in order to allow access to the connection device.

9 Claims, 4 Drawing Sheets

APPARATUS FOR MAKING A PROSTHETIC SOCKET

BACKGROUND OF THE INVENTION

1. Technical Field

The present invention relates generally to a method and apparatus for making a prosthetic socket for an amputated limb and specifically a prosthetic socket. More particularly, the present invention relates to a method and apparatus for manufacturing a prosthetic socket of plastic material using a vacuum-forming technique which allows prosthetic components to become an integral part of the socket.

2. Background Art

Often, a prosthesis is required to assist in restoring an amputee's ability to accomplish many of life's daily tasks. In the case of lower extremity amputations such as the loss of a leg, the prosthesis allows the amputee to stand, walk and run by providing a mechanical extension to the residual limb or stump. Such a prosthesis may comprise an artificial foot connected to an artificial limb shaft with a custom-fitted socket and an elastic sleeve at one end which fits over the residual limb for securing the socket to the residual limb. One of the most important aspects of these prosthesis is strength socket design, the socket being the load-bearing interface between the residual limb and the mechanical support system.

Because each socket must be custom-fitted to the individual patient, socket design and fabrication have been heretofore quite expensive and time-consuming. One technique commonly used to make prosthetic sockets has been to drape a sheet of heated plastic over a positive cast of the residual limb, manually forming the plastic to conform to the contours of the cast. This technique, known as "drape-forming" usually requires two persons and a large degree of manual skill. Further, it often results in significant amounts of wasted plastic and nonuniform forming.

Another technique previously disclosed has been to provide a generally conical, hollow socket preform of memory plastic material which is then placed over a positive cast of the residual limb, the combination being placed in an oven and heated sufficiently to induce shrinkage of the preform onto the cast surface to create a semi-finished socket. This technique, known as "shrink-forming", takes advantage of the characteristics of such memory plastic materials, in particular their tendency to return to their original shape when reheated.

Although shrink-forming offers a more efficient, less labor- and skill-intensive method of socket fabrication than drape-forming, the basic method as described above suffers from several problems. First, the preform may develop imperfections or even perforations during heating at the points of initial contact with the positive cast. This is due to the temperature differential between the cast and the preform during heating, with the cast acting as a heat sink at these points of initial contact. Second, the conventional convection-type ovens presently used in shrink-forming result in nonuniform heating of the preform which in turn results in nonuniform shrinkage of the preform over the cast. Finally, the degree of shrinkage of presently available preforms is less than optimal for these purposes, although this deficiency may be somewhat compensated for by applying a vacuum to the preform/cast interface to help conform the preform to the contours of the cast.

It is believed that the root of the last-mentioned problem lies not so much with the shrink-forming technique but rather with the preform itself. A particularly advantageous method of producing the socket preform utilizes blowmolding, offering fewer steps than other techniques such as injection molding. Blowmolding in such an application involves extruding heated plastic through a mandrel and die to form a parison or tube, enclosing the parison within a mold, and injecting air into the parison until it expands to conform to the contours of the inner cavity of the mold. The use of standard blowmolding techniques, however, does not produce a preform product with optimal shrinkage characteristics. Further, standard blowmolding molds often produce an undesirable raised portion or rib on the inner surface of the preform at its upper end. Because of its location, this rub is difficult to remove and often creates a non-uniform area in the final product. Finally, conventional molds also suffer from parison severing at the upper mold interface during blowmolding of plastics that have a high melt flow index.

In order to avoid the heat-sinking effects and the non-uniform shrinkage of the preform over the cast associated with the prior art, U.S. Pat. No. 5,376,129 to Faulkner et al. discloses a heat and vacuum-forming technique for forming a preform over the exterior surface of a cast. This method first preheats the cast to minimize the temperature differential between the cast and the preform, and then the preform is placed over the cast and heated in the oven to shrink the preform over the exterior surface of the cast. A partial vacuum is also applied to the inner chamber of the cast to further conform the preform with the exterior surface of the cast. This method, however, requires an additional step of drilling holes through the cast to allow air to travel from the exterior surface of the cast toward the vacuum formed in the inner chamber of the cast. Furthermore, this method involves a complicated process of heating the cast and preform while simultaneously applying a vacuum to the assembly.

A further problem existing in the presently available socket forming technology relates to the device used for attaching the socket to an artificial limb shaft. The present socket forming techniques require the additional timeconsuming step of removing excess plastic from around the attachment device after the preform is shrunk onto the cast. This step adds additional expense to the already costly prosthesis since it is imperative to provide a clean connection between the attachment device and the artificial shaft in order to provide adequate support for the artificial limb.

Accordingly, there is clearly a need for a method and apparatus for reliably producing a prosthetic socket having an attachment device which is free from plastic material, wherein an additional step of removing the plastic material from the attachment device is not required after the prosthetic socket is formed. It is further desirable to provide a method of forming a prosthetic socket which avoids the problem of nonuniform shrinkage of the preform over the cast and makes for a stronger attachment point for components.

SUMMARY OF THE INVENTION

It is a primary object of the present invention to overcome the aforementioned shortcomings associated with the prior art.

Another object of the present invention is to provide a method and apparatus for forming a prosthetic socket having an attachment device which does not require the procedure of removing plastic material from the attachment device in order to provide a clean surface to which an artificial limb may be attached.

Yet another object of the present invention is to provide a method and apparatus for forming a prosthetic socket having uniform shrinkage of a plastic material over the cast for the residual limb.

A further object of the present invention is to provide a method and apparatus for forming a prosthetic socket having a more stable connection to an artificial limb.

These as well as additional objects and advantages of the present invention are achieved by providing a vacuum tube assembly for vacuum sealing a layer of plastic material onto a molded cast to form a prosthetic socket. The vacuum tube assembly includes a cylindrical shaft for providing an air path between the molded east and a vacuum suction device. The cylindrical shaft includes a connection device attached to one end of the cylindrical shaft, wherein the connection device is used for affixing the vacuum tube assembly to an attachment device on the prosthetic socket. The attachment device is formed within the prosthetic socket and is affixed to the molded east, wherein the attachment device is the component which connects the prosthetic socket to an artificial limb shaft. A reciprocating cover is also provided on one end of the cylindrical shaft for covering the connection device, so that the reciprocating cover abuts the prosthetic socket when the connection device is affixed to the attachment device. The reciprocating cover is spring-loaded against the cylindrical shaft so that the spring exerts a force against the reciprocating cover toward the prosthetic socket, wherein a force must be exerted against the cover sufficient enough to overcome the spring-load in order to allow access to the connection device.

These as well as additional advantages of the present invention will become apparent from the following description of the invention with reference to the several figures.

DETAILED DESCRIPTION OF THE PREFERRED EMBODIMENT

Figure 1:
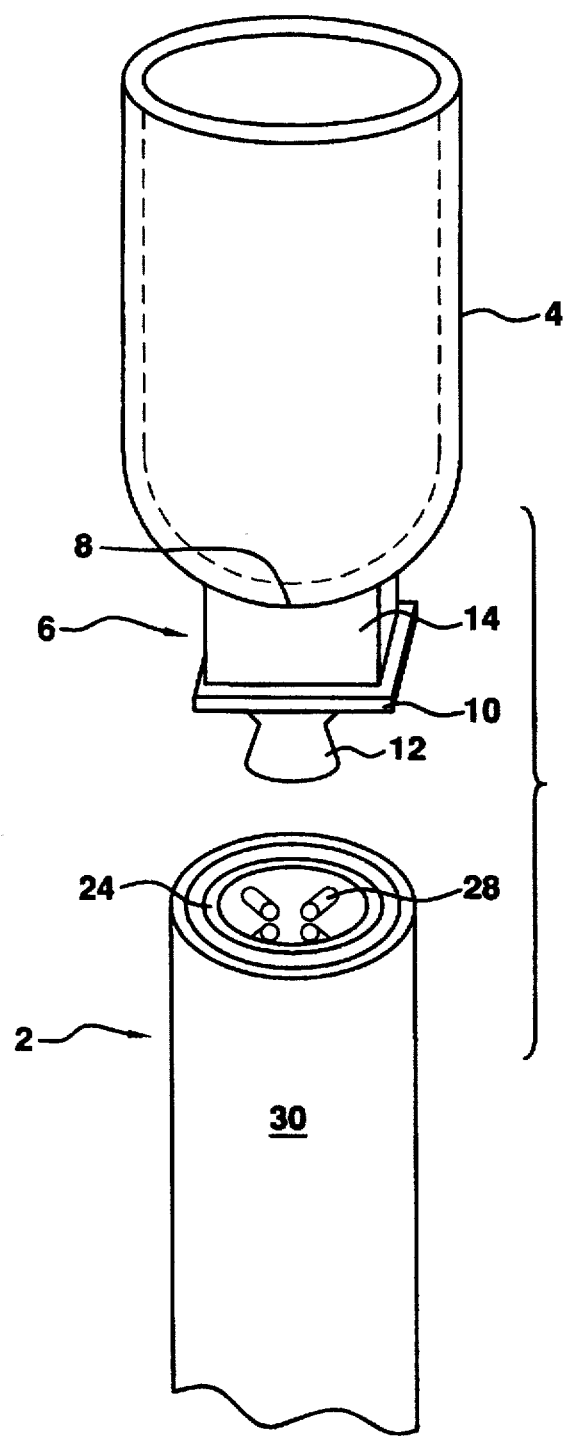
FIG. 1 is a perspective view of the preferred embodiment of the present invention illustrating the vacuum tube assembly and prosthetic socket prior to the formation of the plastic layer thereon.

Referring to FIG. 1, a perspective view illustrates a vacuum tube assembly 2 and a molded cast 4 of an amputated limb in accordance with the preferred embodiment of the present invention. Typically, in order to attach an artificial limb to an amputated limb, a molded cast 4 of the amputated limb must be formed to provide an intermediate connecting structure between the amputated limb and the artificial limb. A mold of the amputated limb is first created to conform to the shape of the amputated limb. Next, the amputated limb cast 4 is fabricated by placing a heated plastic material around the mold so that the plastic material embraces the same shape as the amputated limb. Therefore, the cast 4 may fittingly receive the amputated limb to provide a more comfortable support for the person wearing the cast 4.

In order to connect the cast 4 to an artificial limb, an attachment device 6 is affixed to the distal end 8 of the cast 4 to allow the connection of an artificial limb thereto. The attachment device 6 includes a mounting plate 10, wherein a tapered projection 12 extends from the lower surface of the mounting plate 10. The tapered projection 12 is the portion of attachment device 6 to which the artificial limb is attached. In the preferred embodiment of the present invention, the tapered projection 12 is integrally formed with mounting plate 10 so that the tapered projection 12 may withstand the forces exerted between the weight of the person wearing the cast 4 and the artificial limb. Furthermore, a metallic substance is preferably used in manufacturing the mounting plate 10 and tapered projection 12 in order to provide the necessary strength and durability of the tapered projection in view of the above-described forces exerted on the attachment device 6. However, it is understood by those skilled in the art that the tapered projection 12 may be formed separately from the mounting plate 10 as long as the projection 12 is securely fastened to the mounting plate 10. Further, while a metallic substance has been described as the preferable composition of the tapered projection 12 and mounting plate 10, any substance which can withstand the forces described above and hereinafter can be utilized in conjunction with the preferred embodiment of the present invention.

The attachment device 6 also includes a foam material 14 located on the upper surface of the mounting plate 10 which allows the mounting plate 10 to be attached to the cast 4. The foam material 14 may be affixed to the mounting plate 10 by any suitable adhesive. Similarly, the foam material 14 is affixed to the distal end 8 of the cast 4 (or suitable inner liner) using a suitable adhesive, whereby the foam material 14 provides a tackier surface to adhere to the cast 4 than the surface of mounting plate 10 would provide. The upper portion of the foam material 14 is further shaped to have the same contour as the distal end 8 of the cast 4 in order to provide a better contacting surface between the foam material 14 and the cast 4. The foam material 14 is comprised of a lightweight foam substance in order to minimize the weight of the attachment device 6, yet firm enough not to distort because of heat and vacuum pressure. The adhesive affixing the attachment device 6 to the cast 4 does not have to form a permanent bond between the two surfaces, since this is only a preliminary step of attaching the attachment device to the cast 4. A process of overlaying a plastic material over the cast 4 and attachment device 6 is subsequently performed for permanently affixing the attachment device 6 to the cast 4 thereby forming a prosthetic socket, described in further detail hereinbelow.

Figure 2:
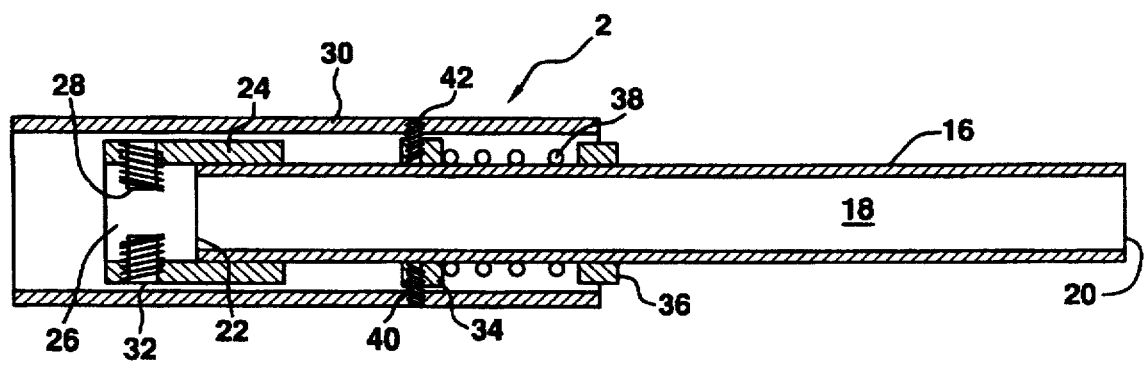
FIG. 2 is a sectional side view of the vacuum tube assembly in accordance with the preferred embodiment of the present invention.
Figure 3:
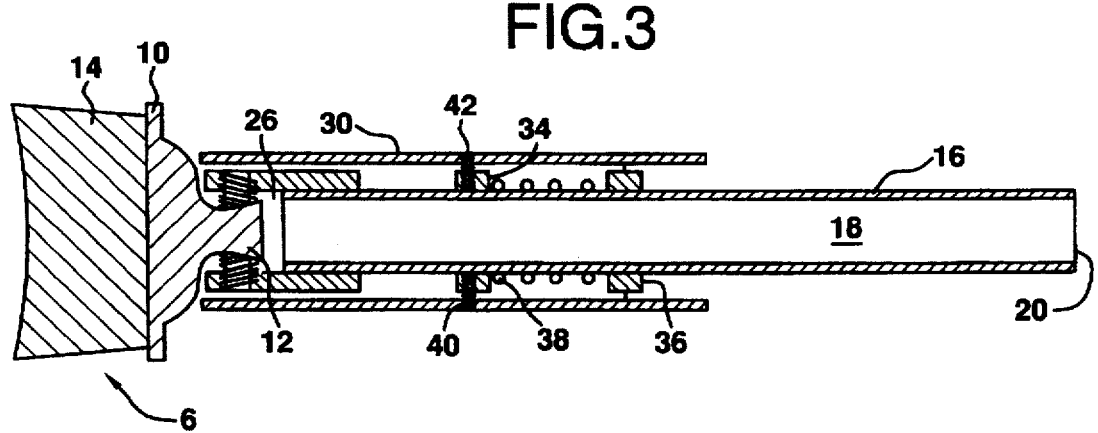
FIG. 3 is a sectional side view of the vacuum tube assembly connected to the attachment device in accordance with the preferred embodiment of the present invention.

The preferred method of forming the plastic overlayer on the cast 4 and attachment device 6 utilizes a vacuum tube assembly 2 illustrated in FIG. 1, and in greater detail in a cross-section view in FIGS. 2 and 3. The vacuum tube assembly 2 enables a prosthetic socket to be formed which does not require a procedure for removing excess plastic material from the attachment device 6 after formation is complete.

The vacuum tube assembly 2 includes a cylindrical shaft 16 having a central passage 18 extending from one end 20 of the shaft 16 to the other end 22. The central passage 18 provides a pathway for air flow between the two ends, wherein a vacuum suction device is attachable to end 20 while the attachment device 6 is attachable to end 22. Therefore, the vacuum tube assembly 2 will pull air from the end 22 of the cylindrical shaft 16 through central passage 18 and exit end 20. A connection device 24 is affixed to the end 22 of cylindrical shaft 16 for attaching the shaft 16 to the tapered projection 12 of mounting plate 10. The connection device 24 is of generally the same shape as shaft 16, having a passage 26 extending through its center for allowing gaseous communication between the central passage 18 and the air surrounding tapered projection 12. A plurality of screws 28 are also threadingly engaged in the connection device 24, whereby the screws 28 extend through apertures 32 in the connection device 24. The screws 28 may be tightened to abut tapered projection 12 into order to secure the connection device 24 to the tapered projection 12, and the outward tapering of projection 12 prevents the connection device 24 from disengaging with the projection 12 20 without the screws 28 being loosened. In the preferred embodiment, four screws 28 are utilized in the connection device 24 with the screws being positioned equidistant from one another around the perimeter of the connection device 24. While the connection device 24 and cylindrical shaft 16 are described as separate components in the preferred embodiment of the present invention, it is understood that the connection device 24 and cylindrical shaft 16 could be integrally formed in a unitary construction.

The vacuum tube assembly 2 also includes a cylindrical outer sleeve 30 which surrounds the outer surface of the end 22 of the cylindrical shaft 16, and further extends beyond the end 22 to additionally cover connection device 24. The sleeve 30 is open at both ends to allow the sleeve to reciprocate about the surface of cylindrical shaft 16, and this open end configuration allows air to travel through the sleeve 30 and into central passage 18. Additionally provided on the outer surface of cylindrical shaft 16 are a pair of cylindrical collars 34 and 36. Collar 36 is affixed to shaft 16 in a manner such that the collar 36 remains stationary with respect to the shaft 16. In the preferred embodiment, the collar 36 includes an inwardly directed screw which may be adjusted to frictionally engage the shaft 16 in order to secure the collar 36 to the shaft 16. By affixing the collar 36 to the shaft 16 in this manner, the collar 36 may be relocated from one stationary position to another stationary position as desired. However, the collar 36 may be affixed to the shaft 16 by other similar means or may be permanently attached to the shaft 16. The second collar 34, however, is not affixed to the cylindrical shaft 16, but rather may travel in a reciprocating motion about the surface of the shaft 16.

A spring 38 is further provided about the surface of the cylindrical shaft 16 positioned between collars 34 and 36, so that one end of the spring 38 contacts collar 34 while the other end of the spring 38 contacts collar 36. Therefore, the motion of collar 34 toward stationary collar 36 is opposed by the force exerted by spring 38, since the spring 38 must be compressed in order for reciprocating collar 34 to move toward stationary collar 36. The reciprocating motion of the collar 34 in the direction away from that of collar 36 is restricted by a movement inhibiting device positioned on the surface of shaft 16. The movement inhibiting device is placed on the opposite side of reciprocating collar 34 from stationary collar 36, whereby the force exerted by the spring 38 on reciprocating collar 34 presses the collar 34 to abut the movement inhibiting device.

The reciprocating collar 34 is further affixed to the outer sleeve 30, wherein the sleeve 30 extends around the periphery of both collars 34 and 36. In the preferred embodiment of the present invention, a plurality of screws 40 extend through apertures 42 in the outer sleeve 30 and threadingly engage with reciprocating collar 34 in order to secure the outer sleeve 30 to the collar 34. However, it is understood by those skilled in the art that outer sleeve 30 may be affixed to reciprocating collar 34 by any device which securely fastens the outer sleeve 30 to the collar 34. Accordingly, the outer sleeve 30 also reciprocates, along with collar 34, about the outer surface of cylindrical shaft 16. When spring 38 is in its normal position forcing reciprocating collar 34 against the movement inhibiting device, the outer sleeve covers both collars 34 and 36 and extends to further cover connection device 24.

Therefore, in order to secure the vacuum tube assembly 2 to tapered projection 12, the outer sleeve 30 must be forced toward end 20 of the cylindrical shaft 16 in order to allow access to connection device 24. Enough force must be exerted against the outer sleeve 30, and in turn reciprocating collar 34, to overcome the force being exerted by spring 38 resisting compression. Once sufficient force is applied, the spring 30 will compress and the outer sleeve will traverse about the outer surface of shaft 16 toward end 20, thus exposing connection device 24. The screws 32 incorporated within connection device 24 may then be tightened to frictionally engage tapered projection 12, as illustrated in FIG. 3, to secure the vacuum tube assembly to tapered projection 12. Once the vacuum tube assembly 2 is secured to tapered projection 12, the force being exerted against outer sleeve 30 to overcome spring 38 is ceased, and the spring 38 will force reciprocating collar 34 back towards end 22 of shaft 16. Thus, outer sleeve 30 will then travel about the surface of shaft 16 away from end 20 until the outer sleeve 30 abuts mounting plate 10. The outer sleeve 30 will come into contact with mounting plate 10 before reciprocating collar 34 contacts the movement inhibiting device, so that the contact between mounting plate 10 and outer sleeve 30 will prevent reciprocating collar 34 from abutting the movement inhibiting device. Once the vacuum tube assembly 2 is attached to the tapered projection 12 as described above and the outer sleeve 30 is abutting mounting plate 10, the process of overlaying a plastic material over the cast 4 and attachment device 6 to thereby form the prosthetic socket is ready to be performed.

Figure 4:
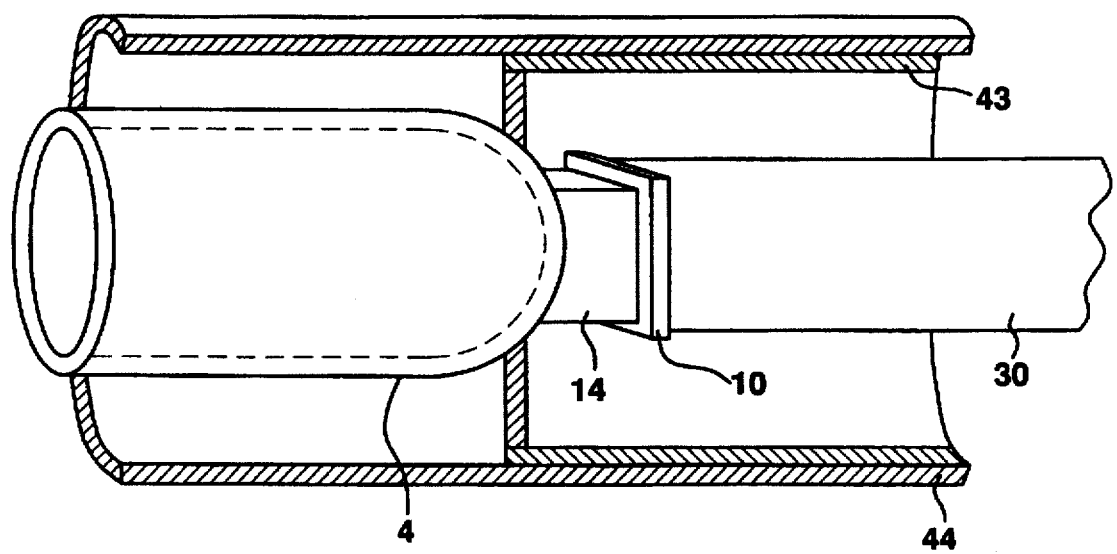
FIG. 4 is a perspective view of the prosthetic socket and vacuum tube assembly illustrating the plastic layer being wrapped therearound.
Figure 5:
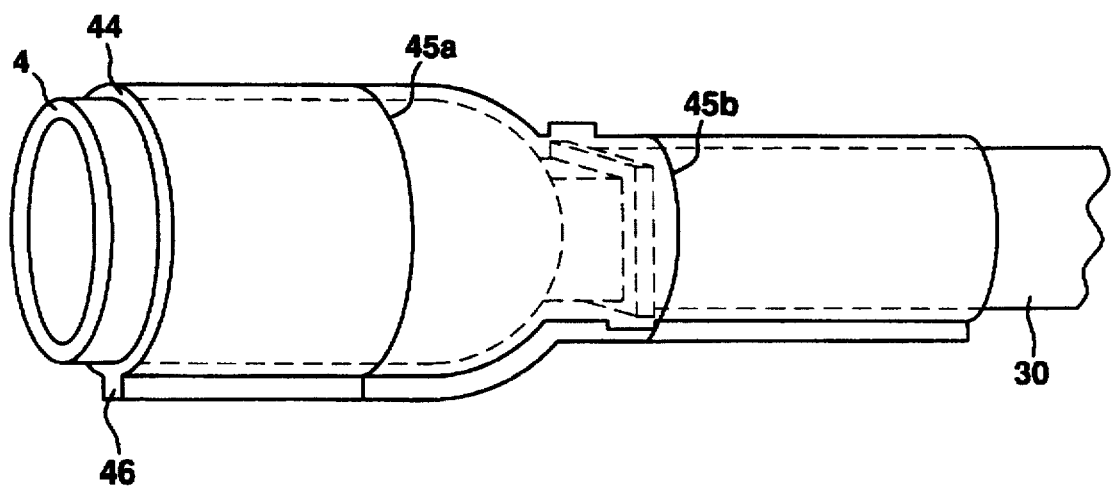
FIG. 5 is a perspective view of the prosthetic socket and vacuum tube assembly having the plastic layer formed therearound.

Referring now to FIGS. 4 and 5, the process of overlaying the plastic material will be described in greater detail. A sheet of plastic material 44 is first heated into a pliable state. A sheet of reinforcing material 43 can also be added to the sheet of plastic material 44 to strengthen the component attachment point, wherein the reinforcing sheet 43 is preferably metal. The reinforcing sheet 43 is bonded to the plastic sheet 44 by heating the reinforcing sheet 43 to the same temperature as the heated pliable plastic sheet 44, and then the two sheets 43 and 44 are thermobonded together in an oven or other heating device by lying the reinforcing sheet 43 on top of the heated plastic sheet 44. The heated plastic sheet 44 and reinforcing sheet 43 are then wrapped around the attachment device 6, a portion of the cast 4, and a portion of the outer sleeve 30. The reinforcing sheet 43 being positioned between the plastic sheet 44 and mounting plate 10, foam material 14 and cast 4, where the reinforcing sheet 43 extends from outer sleeve 30 to cast 4 approximately one to three inches above mounting plate 10. The plastic sheet 44 is wrapped around the full perimeter of these components until the end of the plastic sheet 44 is joined with the beginning of the plastic sheet 44, where the two ends of the pliable plastic sheet 44 are molded together at 46 to fully encapsulate the components. Any excess portion of plastic sheet 44 extending beyond where the plastic sheet 44 is joined together at 46 may be cut off, leaving a rib 46. Thereafter, a suction device attached to end 20 of cylindrical shaft 18 is activated to begin a flow of air through shaft 16 toward the suction device at end 20. Any air which is present underneath of the sheet of plastic material 44, between the plastic material 44 and cast 4, attachment device 6 and sleeve 30, will be removed and forced between the contacting surfaces of outer sleeve 30 and mounting plate 10, through passage 26 in connection device 24, further through central passage 18 and finally to the suction device at the end 20 of shaft 16. Removing the air underneath of plastic sheet 44 effectively shrinks the plastic sheet 44 onto the components therebeneath, so that when the heated plastic sheet 44 cools it will result in an airtight bond between the plastic sheet 44 and the components therebeneath.

In order to increase the strength and effectiveness of the vacuum created, two strings 45a and 45b may be tied around the plastic sheet 44 after it has been wrapped around the components. A first string 45a is tied around the plastic material 44 surrounding the molded cast 4, thereby tightly pressing the plastic sheet 44 against the cast 4 and preventing the flow of air between plastic sheet 44 and the cast 4 underneath of the string 45a. A second string 45b is tied around the plastic material 44 surrounding the sleeve 30, thereby tightly pressing the plastic sheet 44 against the sleeve 30 and preventing the flow of air between plastic sheet 44 and the sleeve 30 underneath of the string 45b. Therefore, a closed air pocket is formed between the two strings 45a and 45b with the only flow of air traveling from the closed air pocket to the suction device through passage 18 in shaft 16. This air path is achieved because the area between the abutting surfaces of the mounting plate 10 and outer sleeve 30 is permeable to air. However, even though an air-tight seal is not formed, the outer sleeve 30 is being forced against mounting plate 10 by spring 38 tightly enough that there is not sufficient distance between the outer sleeve 30 and the mounting plate 10 to allow the flow of the pliable plastic material therebetween. Therefore, no plastic material 44 comes into contact with the tapered projection 12 during the plastic overlay procedure.

In addition to increasing the effectiveness of the vacuum, the strings 45a and 45b also serve to score the plastic sheet 44 providing a breaking point where the plastic sheet 44 outside of the strings may be removed. Tying the strings 45a and 45b tightly around the plastic sheet 44 makes the pliable plastic sheet 44 thinner beneath the strings 45a and 45b, so that excess plastic material may be easily removed leaving only the portion of the plastic sheet 44 between the two strings 45a and 45b. Since the strings 45a and 45b create the closed air pocket between them, the portion of the plastic sheet 44 outside of the strings 45a and 45b will not shrink when the vacuum is applied to the plastic sheet 44. Therefore, the portion of the plastic sheet outside of the strings 45a and 45b can be easily removable. Accordingly, the string 45a wrapped around cast 4 may be varyingly positioned to provide the desired length of the plastic material 44 on each specific prosthetic socket formed depending upon the support needed. The other string 45b is wrapped around outer sleeve 30 adjacent to where the outer sleeve 30 abuts mounting plate 10, which allows most of the plastic material 44 on the sleeve 30 side of mounting plate 10 to be easily removed.

Once the vacuum has removed all of the air in the closed air pocket, the strings 45a and 45b are removed from around the plastic material 44 and the plastic material 44 is left to cool and harden. Once cooled, the excess plastic material outside of where the strings 45a and 45b were tied is removed by cutting the thinned plastic material where the strings 45a and 45b were tied and the excess plastic material is removed. The vacuum tube assembly 2 is now ready to be removed from the finished prosthetic socket 50. The outer sleeve 30 is forced toward the end 20 of shaft 16 to allow access to connection device 24, wherein the screws 28 are loosened to disengage from tapered projection 12. The formation process for the prosthetic socket 50 is now complete.

Figure 6:
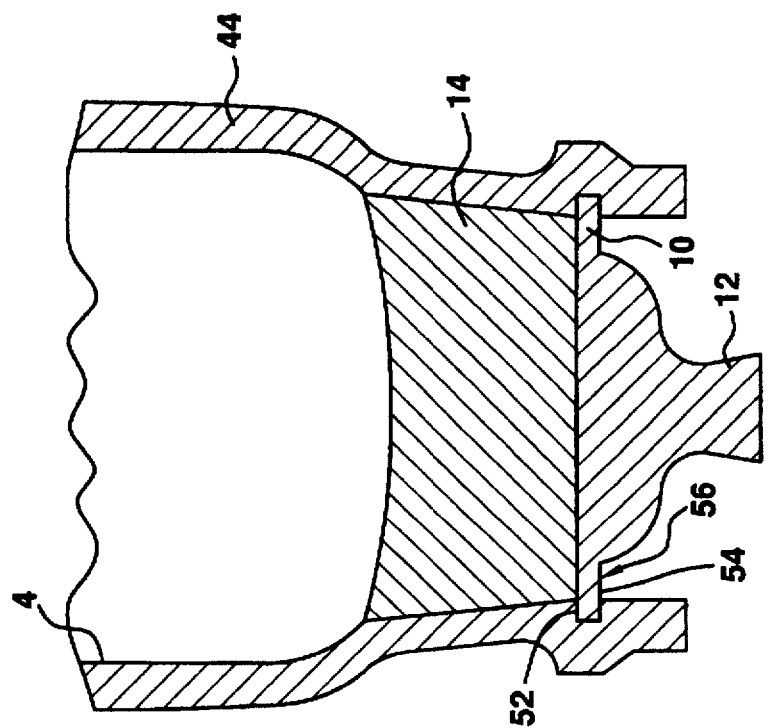
FIG. 6 is a sectional side view of the prosthetic socket in accordance with the preferred embodiment of the present invention.
Figure 7:
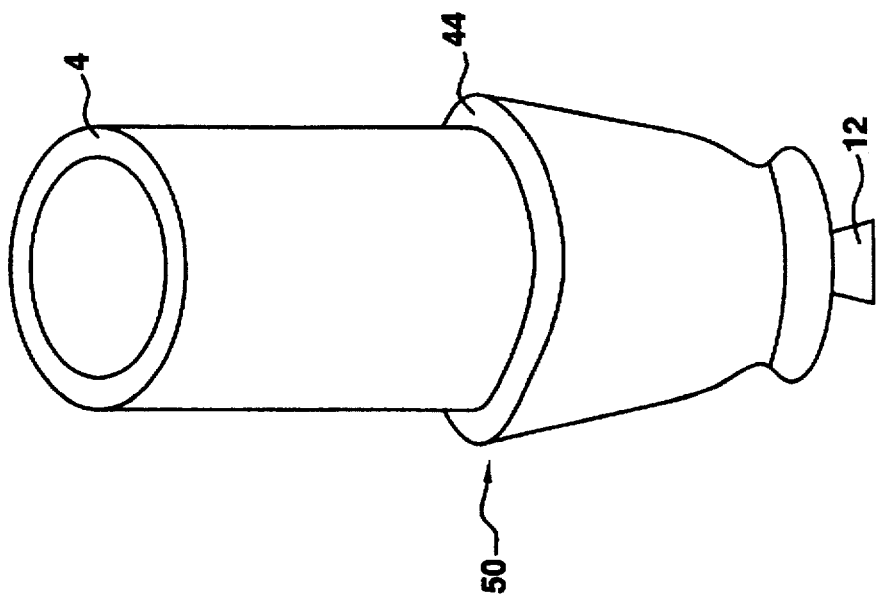
FIG. 7 is a perspective view of the prosthetic socket in accordance with the preferred embodiment of the present invention.

Referring now to FIGS. 6 and 7, the completed prosthetic socket 50 will be described in greater detail. As can be seen from the Figures, the layer of plastic material 44 conforms to the shape of the cast 4, foam material 14 and mounting plate 10. The thickness of the plastic layer 44 is most effective within the range of 1/8 inch to 1/2 inch, and in the preferred embodiment of the present invention should comprise a thickness of 3/16 inch. For the average individual wearing this prosthetic socket 50, it has been found that 3/16 inch provides the optimal thickness for the plastic layer 44 taking into account certain design characteristics, such as strength and weight of the socket 50. For heavier individuals, the thickness of the plastic layer is preferably 1/4 inch to provide greater strength and stability in the prosthetic socket 50.

It can be further seen from FIG. 6 that mounting plate 10 has both a proximal shoulder 52 and a distal shoulder 54. The proximal shoulder 52 is formed by attaching a foam material 14 to the mounting plate 10, wherein the foam material 14 includes a slightly smaller perimeter than the mounting plate 10 and the distance between the two perimeters creates the proximal shoulder 52. The distal shoulder 54 is integrally formed with the mounting plate 10. It is important that the proximal shoulder 52 is not made to be too large, because the width of proximal shoulder 52 can affect the strength of the plastic layer 44. Since the plastic layer 44 conforms to the shape of the foam material 14 and mounting plate 10, a wide proximal shoulder 52 would cause the plastic layer 44 to be drawn into the shoulder area. If the plastic layer 44 is drawn into too deep of a proximal shoulder 52, the plastic layer 44 would make a 90° turn around the mounting plate 10 and into proximal shoulder 52. Sharp turns of this sort in the plastic layer 44 cause the plastic to weaken at these points in the layer 44. Therefore, it is important to minimize the angles of direction the plastic layer 44 must turn in order to prevent weak stress points from developing. Accordingly, the foam material 14 must be formed so as not to create a deep proximal shoulder 52 on the mounting plate 10.

A recessed socket 56 is also formed around the distal shoulder on the mounting plate 10. Since the outer sleeve 30 abuts the distal shoulder 54 of mounting plate 10 during the formation of the plastic layer 44, no portion of the plastic layer 44 is formed on the tapered projection 12. Furthermore, when the excess plastic material is cut from the plastic layer 44, the cut is made a slight distance below the distal shoulder 54 portion of mounting plate 10 so that the plastic layer extends beyond shoulder 54. Additionally, the diameter of the outer sleeve 30 is smaller than the diameter of mounting plate 10, which allows the plastic sheet 44 to be formed on a portion of distal shoulder 54. The portion of the plastic sheet 44 extending beyond distal shoulder 54 forms a recessed socket 56 between that portion of the plastic sheet 44 and tapered projection 12. The recessed socket 56, free from plastic material, provides access to tapered projection 12 without having to first clean plastic material from the projection 12, wherein tapered projection 12 is where the prosthetic socket 50 is attached to an artificial limb. Since no plastic material needs to trimmed from the surface of tapered projection 12, this method of manufacturing a prosthetic socket 50 results a simpler and cleaner way to provide access to the attachment device 6 of the prosthetic socket 50.

The structure of the preferred embodiment of the present invention provides a stronger connection between the attachment device 6 and cast 4 than could be achieved in the past. The plastic layer 44 affixing the attachment device 6 to the cast 4 resists any circumferential forces that may be exerted on the attachment device 6, because the plastic layer 44 surrounds the perimeter of both the cast 4 and attachment device 6. Since the layer of plastic 44 extending over cast 4 also extends over the proximal shoulder 52 and distal shoulder 54 of mounting plate 10, the plastic layer 44 resists any upward and downward forces that may be exerted on the attachment device 6.

Furthermore, the structure of the preferred embodiment provides a more stable connection between the prosthetic socket 50 and an artificial limb due to the recessed socket 56 formed in the attachment device 6. When the artificial limb connects to tapered projection 12, the artificial limb may receive additional lateral support from the portion of plastic sheet 44 that extends beyond the distal end 54 of mounting plate 10. This added support would provide a more stable connection between the prosthetic socket 50 and artificial limb than the tapered projection 12 could provide by itself. Additionally, the foam material 14 may be removed from the prosthetic socket after molding is complete in order to lighten the prosthetic socket 50 without affecting its stability.

As can be seen by the foregoing, a prosthetic socket formed in accordance with the present invention will provide an improved method of forming a plastic layer on a cast and an attachment device without the need for trimming excess plastic from the attachment device. Moreover, by forming a prosthetic socket in accordance with the present invention, a stronger support is provided between the prosthetic socket and artificial limb.

While the present invention has been described with reference to a preferred embodiment, it should be appreciated by those skilled in the art that the invention may be practiced otherwise than as specifically described herein without departing from the spirit and scope of the invention. Specifically, while the vacuum tube assembly 2 discussed above included most of its components described as being cylindrical, it is understood that these components, such as shaft 16, sleeve 30, connection device 24 and collars 34 and 36, may comprise any shape which allows them to function in accordance with the present invention discussed above. It is, therefore, to be understood that the spirit and scope of the invention be limited only by the appended claims.

What is claimed is:

1. A vacuum tube assembly for vacuum sealing a plastic layer on a prosthetic socket, comprising:

a cylindrical shaft for providing an air path for the vacuum tube assembly;

connecting means attached to one end of said cylindrical shaft; said connecting means being further attachable to an attachment means in the prosthetic socket; and cover means attached to said cylindrical shaft' for covering said connecting means.

2. The vacuum tube assembly described in claim 1, wherein said cover means abuts said attachment means.

3. The vacuum tube assembly described in claim 1, wherein said cover means may reciprocate about an outer surface of said cylindrical shaft.

4. The vacuum tube assembly described in claim 3, wherein said attachment means is recessed within the plastic layer.

5. The vacuum tube assembly described in claim 4, wherein said cover means forms a socket in the plastic layer around said attachment means.

6. The vacuum tube assembly described in claim 3, further comprising a spring means for applying a resistive force against the reciprocating motion of said cover means.

7. The vacuum tube assembly as defined in claim 6, wherein said spring means exerts a force against said cover means to maintain said cover means is a position abutting said attachment means.

8. The vacuum tube assembly as defined in claim 7, wherein said cover means may be reciprocated about the outer surface of said cylindrical shaft to expose said connecting means by applying a force against said cover means sufficient enough to overcome said spring means.

9. The vacuum tube assembly as defined in claim 1, wherein said connection means includes a plurality of inwardly directed screw means for attaching the connecting means to said attachment means.

* * * * *